(12) United States Patent
Taylor et al.

(10) Patent No.: US 10,588,778 B2
(45) Date of Patent: Mar. 17, 2020

(54) MOBILE THERMAL SYSTEM

(71) Applicant: Stryker Corporation, Kalamazoo, MI (US)

(72) Inventors: Gregory S. Taylor, Kalamazoo, MI (US); Christopher John Hopper, Kalamazoo, MI (US); Roy E. Holmberg, III, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 325 days.

(21) Appl. No.: 15/460,988

(22) Filed: Mar. 16, 2017

(65) Prior Publication Data

US 2017/0266036 A1 Sep. 21, 2017

Related U.S. Application Data

(60) Provisional application No. 62/311,054, filed on Mar. 21, 2016.

(51) Int. Cl.
*A61F 7/00* (2006.01)
*F28F 27/02* (2006.01)

(52) U.S. Cl.
CPC .......... *A61F 7/0085* (2013.01); *A61F 7/0053* (2013.01); *F28F 27/02* (2013.01); *A61F 2007/0086* (2013.01); *F28F 2280/02* (2013.01)

(58) Field of Classification Search
CPC ............ A61F 7/0085; A61F 2007/0054; A61F 2007/0056
See application file for complete search history.

(56) References Cited

U.S. PATENT DOCUMENTS 4,118,946 A 10/1978 Tubin
5,172,511 A 12/1992 Smith et al.
(Continued)

FOREIGN PATENT DOCUMENTS

CN 2251310 Y 4/1997
WO 2007/005026 A1 1/2007

OTHER PUBLICATIONS

Wikipedia Contributors. "Evaporative Cooler." Wikipedia, The Free Encyclopedia. Feb. 24, 2017. https://en.wikipedia.org/wiki/Evaporative_cooler (last modified Oct. 18, 2015).
(Continued)

*Primary Examiner* — Kaitlyn E Smith
(74) *Attorney, Agent, or Firm* — Warner Norcross + Judd LLP (57) ABSTRACT

A thermal control unit for controlling the temperature of a patient includes a fluid circulation channel with an inlet and outlet, a first heat exchanger, a controller, and a cartridge receptacle. The controller controls the first heat exchanger to adjust the temperature of the circulating fluid toward a desired temperature. The cartridge receptacle is adapted to receive a cartridge having a second heat exchanger and to allow fluid to flow from the cartridge into the fluid circulation channel of the thermal control unit. The cartridge may include a vacuum chamber and a coolant whereby the expansion of the coolant into the vacuum chamber cools the fluid in the cartridge. Flow of the coolant in the vacuum chamber may be automatically initiated upon insertion of the cartridge into the cartridge receptacle, or by other means.

23 Claims, 3 Drawing Sheets

(56) References Cited

U.S. PATENT DOCUMENTS

| | | | |
|---|---|---|---|
| 5,482,355 A | 1/1996 | Franzen, Jr. | |
| 5,486,206 A | 1/1996 | Avery | |
| 5,647,051 A | 7/1997 | Neer | |
| 5,845,501 A | 12/1998 | Stonehouse et al. | |
| 5,948,012 A | 9/1999 | Mahaffey et al. | |
| 6,197,045 B1 | 3/2001 | Carson | |
| 6,371,976 B1 | 4/2002 | Vrzalik et al. | |
| 6,699,266 B2 | 3/2004 | Lachenbruch et al. | |
| 6,878,156 B1 | 4/2005 | Noda | |
| 7,008,445 B2 | 3/2006 | Lennox | |
| 7,106,662 B1 | 9/2006 | Acker, Jr. | |
| 7,972,287 B2 | 7/2011 | Stewart et al. | |
| 8,512,263 B2 | 8/2013 | Gammons | |
| 8,657,864 B2 | 2/2014 | Rein et al. | |
| 8,801,272 B2 | 8/2014 | Bieberich et al. | |
| 8,968,378 B2 | 3/2015 | Ginsburg et al. | |
| 9,289,110 B2* | 3/2016 | Woolford | A61B 1/00039 |
| 2006/0005314 A1 | 1/2006 | Lee | |
| 2006/0287697 A1* | 12/2006 | Lennox | A61F 7/0085 |
| | | | 607/96 |
| 2006/0293734 A1* | 12/2006 | Scott | A61F 7/12 |
| | | | 607/105 |
| 2007/0191918 A1* | 8/2007 | MacHold | A61M 25/10 |
| | | | 607/105 |
| 2007/0288074 A1 | 12/2007 | Cazzini | |
| 2008/0060374 A1 | 3/2008 | Gammons et al. | |
| 2008/0234619 A1* | 9/2008 | Fausset | A61F 7/12 |
| | | | 604/4.01 |
| 2008/0255644 A1 | 10/2008 | Carson | |
| 2009/0069796 A1* | 3/2009 | Oskin | A61B 18/04 |
| | | | 606/27 |
| 2009/0125014 A1* | 5/2009 | Bouthillier | A61B 18/04 |
| | | | 606/34 |
| 2010/0274331 A1 | 10/2010 | Williamson et al. | |
| 2011/0022136 A1* | 1/2011 | Scott | A61F 7/12 |
| | | | 607/105 |
| 2012/0109267 A1* | 5/2012 | Fausset | A61F 7/007 |
| | | | 607/96 |
| 2012/0157983 A1* | 6/2012 | Bouthillier | A61B 18/04 |
| | | | 606/27 |
| 2012/0165804 A1* | 6/2012 | Newell | A61B 18/04 |
| | | | 606/27 |
| 2013/0085552 A1 | 4/2013 | Mandel | |
| 2013/0098069 A1 | 4/2013 | Collins | |
| 2013/0158443 A1 | 6/2013 | Kraal et al. | |
| 2014/0046411 A1* | 2/2014 | Elkins | A61F 7/00 |
| | | | 607/104 |
| 2014/0114235 A1* | 4/2014 | Oskin | A61B 18/04 |
| | | | 604/22 |
| 2014/0172050 A1* | 6/2014 | Dabrowiak | A61F 7/0085 |
| | | | 607/106 |
| 2014/0222121 A1 | 8/2014 | Spence et al. | |
| 2014/0265502 A1 | 9/2014 | Hough et al. | |
| 2014/0309630 A1* | 10/2014 | Bouthillier | A61B 18/04 |
| | | | 606/27 |
| 2014/0358201 A1* | 12/2014 | Scott | A61F 7/12 |
| | | | 607/105 |
| 2015/0018905 A1* | 1/2015 | Nofzinger | A61F 7/007 |
| | | | 607/109 |
| 2015/0223972 A1* | 8/2015 | Dabrowiak | A61F 7/0085 |
| | | | 607/106 |
| 2015/0230973 A1* | 8/2015 | Dabrowiak | A61F 7/0085 |
| | | | 607/105 |
| 2015/0230974 A1* | 8/2015 | Pistor | A61F 7/0085 |
| | | | 607/105 |
| 2015/0230975 A1* | 8/2015 | Dabrowiak | A61F 7/0085 |
| | | | 607/105 |
| 2015/0366367 A1 | 12/2015 | Augustine et al. | |
| 2016/0128864 A1* | 5/2016 | Nofzinger | A61F 7/007 |
| | | | 607/109 |
| 2016/0287434 A1* | 10/2016 | Dabrowiak | A61F 7/0085 |
| 2016/0287435 A1* | 10/2016 | Pamichev | A61F 7/0085 |
| 2016/0354234 A1* | 12/2016 | Dabrowiak | A61F 7/0085 |
| 2017/0035604 A1* | 2/2017 | Dabrowiak | A61F 7/0085 |
| 2018/0207024 A1* | 7/2018 | Dabrowiak | A61F 7/0085 |
| 2018/0214301 A1* | 8/2018 | Fojtik | A61F 7/0085 |
| 2018/0289539 A1* | 10/2018 | Stull | A61F 7/123 |
| 2018/0311072 A1* | 11/2018 | Pamichev | A61F 7/0085 |

OTHER PUBLICATIONS

Arctic Sun 2000, Medivance Arctic Sun Temperature Management System Operator's Manual, 2007.

Gaymar Medi-Therm III, Hyper/Hypothermia Machine Ref MTA7912 Service Manual, Nov. 2009.

Arctic Sun 5000, Medivance Service Manual, 2010-2011.

Arctic Sun 5000 Temperature Management System, Medivance Service Manual, Jun. 2013.

Heater-Cooler System 3T, Sorin Group Operating Instructions, Feb. 2015.

Altrix Precision Temperature Management System, Stryker Operations Manual, Dec. 2016.

* cited by examiner

MOBILE THERMAL SYSTEM

CROSS-REFERENCE TO RELATED APPLICATIONS

This application claims priority to U.S. provisional patent application Ser. No. 62/311,054 filed Mar. 21, 2016, by inventor Gregory Taylor and entitled MOBILE THERMAL SYSTEM, the complete disclosure of which is incorporated herein by reference.

BACKGROUND

The present invention relates to a mobile thermal control system for controlling the temperature of circulating fluid which is delivered to one or more thermal pads positioned in contact with a patient.

Thermal control systems are known in the art for controlling the temperature of a patient by supplying temperature-controlled fluid to one or more pads, blankets, or similar structures, that are positioned in contact with a patient. The temperature of the fluid is controlled by a thermal unit that provides fluid to the pads or blankets. After passing through the pads or blankets, the fluid is returned to the control unit where any necessary adjustments to the returning fluid temperature are made before being pumped back to the pad or blanket. In some instances, the temperature of the fluid is controlled to a target temperature, while in other instances the temperature of the fluid is controlled in order to effectuate a target patient temperature. When controlling a patient's temperature, a patient temperature probe may be attached to the control unit in order to provide patient temperature readings as feedback to the control unit so that it can make the necessary temperature adjustments.

When controlling a patient's temperature in a medical facility, such as a hospital, equipment may be used that is generally bulky and not easily moved. When attempting to control a patient's temperature in a medical situation outside of a hospital, it is often not possible to utilize the same bulky equipment that is available at the hospital. Instead, mobile temperature control units are used which often lack one or more features and/or abilities of the temperature control units found in hospitals.

SUMMARY

The present invention provides various improved aspects to a thermal control system that is mobile and adapted to be easily utilized in environments outside of medical facilities. These improved aspects provide the mobile thermal control system with one or more features and/or abilities that are comparable to the features and/or abilities of non-mobile thermal control systems found in medical facilities. In one embodiment, the present invention includes a thermal control unit that takes less time to bring the regulated fluid to the desired temperature, while still being able to maintain a desired target temperature for an extended period of time prior to the patient being brought to a medical facility. In other embodiments, still other features and/or abilities are provided.

According to one embodiment, a thermal control unit is provided that includes a fluid circulation channel, a first heat exchanger, a pump, a controller, and a cartridge receptacle. The fluid circulation channel includes a fluid outlet and a fluid inlet. The fluid outlet is adapted to supply fluid to a thermal transfer device and the fluid inlet is adapted to receive the fluid back from the thermal transfer device. The pump circulates fluid through the fluid circulation path, including from the fluid inlet, through the first heat exchanger, and to the fluid outlet. The controller controls the first heat exchanger such that a temperature of the fluid is changed toward a target temperature. The cartridge receptacle is adapted to receive a cartridge and to allow fluid from within the cartridge to flow into the fluid circulation channel when the cartridge is inserted into the cartridge receptacle. The cartridge includes a second heat exchanger adapted to change the temperature of the fluid toward the target temperature independent of the first heat exchanger.

According to another embodiment, a method of cooling a patient is provided that includes cooling a fluid contained within a cartridge by using a first heat exchanger contained within the cartridge. The cartridge is inserted into a thermal control unit and fluid from the cartridge is transferred to a fluid circulation channel within the thermal control unit. The temperature of the fluid is controlled using a second heat exchanger contained within the thermal control unit. The fluid is supplied to a thermal transfer device in contact with the patient.

According to still another embodiment, a thermal control system for controlling a temperature of a patient is provided. The thermal control system includes a cartridge and a thermal control unit. The cartridge includes a fluid reservoir, a coolant, and a vacuum chamber. The thermal control unit includes a fluid circulation channel, a heat exchanger, a pump, and a controller. The thermal control unit receives fluid from the cartridge that has been cooled by the coolant and pumps the cooled fluid to a thermal transfer device in contact with the patient.

In still another embodiment, a thermal cartridge is provided that includes a fluid reservoir, a coolant, a vacuum chamber, and first and second controls. The first control maintains the coolant separate from the vacuum chamber until the first control is activated. The second control maintains the fluid in the fluid reservoir until the second control is activated. The thermal control cartridge is further adapted to be inserted into a thermal control unit and to thereafter release the fluid from the fluid reservoir into the thermal control unit.

In some embodiments, the first control and/or second control is adapted to be automatically activated upon insertion into the thermal control unit.

According to still other embodiments, the thermal control system is adapted to power the heat exchanger of the control unit via a battery when the patient is located outside of a medical facility, and to power the heat exchanger of the control unit via an electrical outlet when the patient is located within a medical facility, or otherwise positioned within range of an electrical outlet. The heat exchanger of the cartridge is not electrically powered in these embodiments.

In some embodiments, the heat exchanger of the cartridge comprises a vacuum and a coolant that are isolated from each other until activated by a user. Upon activation by the user, the coolant expands into the vacuum and absorbs heat. The coolant is in thermal communication with fluid stored in a fluid reservoir such that the coolant absorbs heat from the fluid.

According to some embodiments, the thermal control unit further includes a temperature sensor in communication with the controller. When so included, the controller controls the first heat exchanger in a closed-loop manner utilizing readings from the temperature sensor in order to change the temperature of the fluid toward a target temperature. The target temperature may be chosen by a user utilizing a control panel on the thermal control unit.

The cartridge supplies all of the fluid for circulating in the fluid circulation channel of the thermal control unit, in at least one embodiment.

In some embodiments, the thermal control unit is portable, the target temperature is lower than the normal human body temperature, and the thermal transfer device is a pad adapted to contact a patient to thereby cool at least a portion of the patient.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
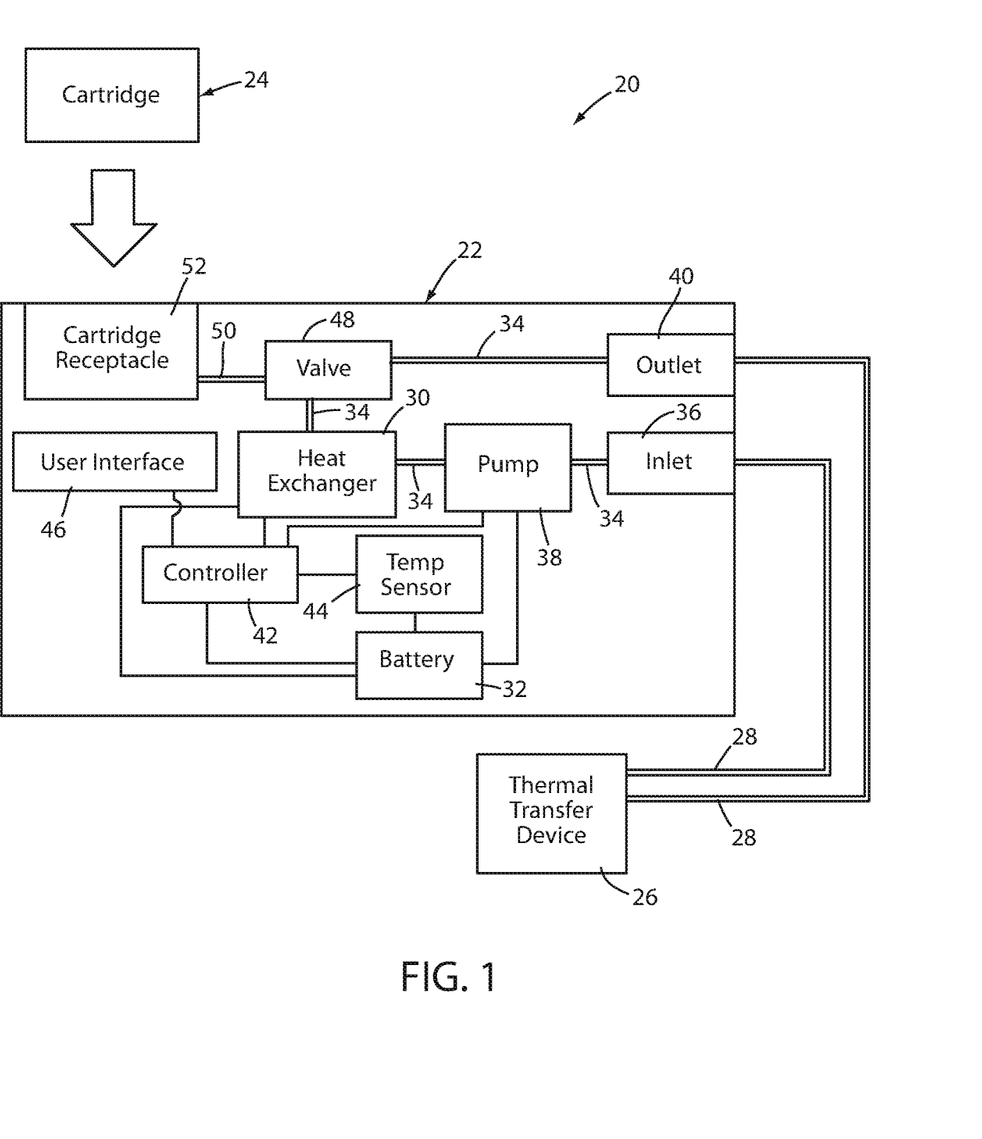
FIG. 1 is a block diagram of a thermal control system according to one aspect of the present invention.

A thermal control system 20 according to one embodiment of the present invention is shown in block diagram form in FIG. 1. Thermal control system 20 includes a thermal control unit 22 and a cartridge 24 adapted to be inserted into and pulled out of thermal control unit 22. Cartridge 24 supplies a cooling fluid to thermal control unit 22 after cartridge 24 is inserted into control unit 22. Thermal control unit 22 pumps the received cooling fluid to a thermal transfer device 26, which is coupled to thermal control unit 22 by way of one or more hoses 28. Thermal transfer device 26 may be a thermal pad, blanket, vest, or other structure that is adapted to be placed in contact with a patient and control the temperature of the patient. The fluid pumped to thermal transfer device 26 is returned back to thermal control unit 22 by one of hoses 28. The returning fluid has its temperature adjusted, as needed, by control unit 22 in order to maintain the fluid temperature at a target temperature and/or to maintain the patient at a target temperature. Thermal control unit 22 adjusts the temperature of the fluid using one or more heat exchangers 30.

By controlling the temperature of the fluid flowing through hose 28 to thermal transfer device 26, the temperature of a patient can be controlled via the close contact of the transfer device 26 with the patient and the resultant heat transfer therebetween. In some embodiments, multiple thermal transfer devices 26 are coupled to thermal control unit 22. In some of those cases where such multiple thermal transfer devices 26 are used, a first thermal transfer device 26 is wrapped around a patient's torso, while second and third thermal transfer devices 26 are wrapped, respectively, around the patient's right and left legs. Other configurations can be used and, as noted, different numbers of thermal transfer devices 26 may be used with thermal control unit 22, depending upon the number of hose connections of the thermal control unit 22.

Thermal control unit 22 is a portable unit that is adapted to be carried by a paramedic, or other personnel, while working outside of a medical facility. In this regard, thermal control unit 22 may include one or more straps (not shown), or other means for enabling a user to easily carry control unit 22 to the location of a patient. Thermal control unit 22 also includes one or more batteries adapted to provide electrical power to thermal control unit 22. In some embodiments, thermal control unit 22 also includes an electrical cord adapted to be plugged into an electric outlet and receive power therefrom when control unit 22 is used in a location that includes an available electrical outlet, such as a medical facility. In this manner, battery 32 provides electrical power while treating the patient in locations outside the medical facility, while an electrical outlet provides electrical power when treating the patients in the medical facility. In some embodiments, battery 32 is a rechargeable battery that can be recharged whenever the electrical cord is plugged into an electrical outlet. In still other embodiments, control unit 22 is adapted to be inductively charged such that it is unnecessary to plug an electrical cord into an outlet for recharging battery 32. Such inductive charging may be carried out in any of the manners disclosed in commonly assigned U.S. patent application Ser. No. 15/040,593 filed Feb. 20, 2016 by inventors Clifford Lambarth et el. and entitled PATIENT SUPPORT WITH ENERGY TRANSFER, the complete disclosure of which is hereby incorporated herein by reference. Other manners of inductive charging may also be used.

Thermal control system 20 is adapted to be able to quickly provide cooling treatment to a patient, as well as to be able to maintain the cooling treatment for as long as it takes to transport the patient to a medical facility. In this regard, thermal control system 20 avoids the problem of allowing the patient to become re-warmed prior to arriving at the medical facility. That is, some prior art thermal control systems, while able to quickly cool a patient, are unable to sustain the patient at the cooled temperature for more than a minimal amount of time. In such prior art systems, if the patient is not soon transported to a hospital or other medical facility, the system is not able to provide further cooling at rates sufficient to maintain the patient at the cooled temperature. As a result, the patient begins warming prior to arrival at the medical facility. This cooling and re-warming prior to arrival at the hospital can, in some cases, be more detrimental to the patient's health than no cooling at all. Thermal control system 20 avoids this undesirable outcome.

The internal components of thermal control unit 22 are shown in more detail in FIG. 1. In addition to heat exchanger 30 and battery 32, thermal control unit 22 includes a fluid circulation path 34 that extends from an inlet 36 to a pump 38, through heat exchanger 30, and from there to an outlet 40. Outlet 40 is adapted to be coupled to a hose 28 to thereby deliver temperature controlled fluid to thermal transfer device 26. Inlet 36 is also adapted to be coupled to a hose 28 to thereby return the temperature controlled fluid to thermal control unit 22 after having passed through the thermal transfer device 26.

Thermal control unit 22 further includes a controller 42 that communicates with heat exchanger 30, pump 38, and one or more temperature sensors 44. Temperature sensors 44 is adapted to sense the temperature of the fluid flowing through circulation path 34 and report the sensed temperature to controller 42. Controller 42 includes any and all electrical circuitry and components necessary to carry out the functions and algorithms described herein, as would be known to one of ordinary skill in the art. Generally speaking, controller 42 may include one or more microcontrollers, microprocessors, and/or other programmable electronics that are programmed to carry out the functions described herein. It will be understood that controller 42 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), Ethernet, etc.

Figure 2:
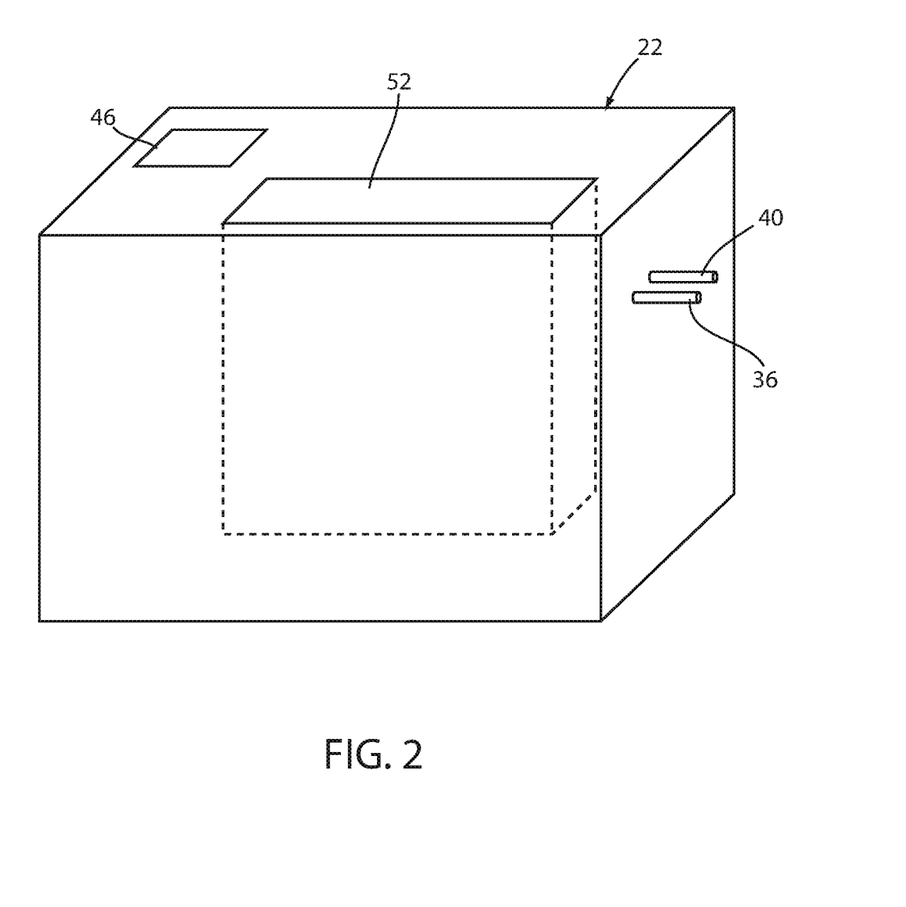
FIG. 2 is a perspective view of one embodiment of a thermal control unit of the thermal control system of FIG. 1.

Controller 42 is also in communication with a user interface 46 (FIGS. 1 & 2). User interface 46 includes one or more controls enabling a user to turn control unit 22 on and off, as well as one or more controls enabling the user to select a target temperature for the fluid delivered to thermal transfer device 26 via outlet 40. In some embodiments, user interface 46 also allows a user to select a target temperature for the patient being treated, rather than a specific target temperature for the fluid. When this feature is present, controller 42 makes automatic adjustments to the temperature of the fluid in order to bring the patient's temperature to the desired patient target temperature.

When the user has selected a target temperature for the fluid, controller 42 utilizes the selected target temperature, as well as the temperature reading from temperature sensor 44, to generate and send commands to heat exchanger 30, as necessary, in order to cool and/or warm the fluid in circulation path 34 so that it meets the selected target temperature. In at least one embodiment, controller 42 implements closed-loop feedback control of heat exchanger 30 using the output from temperature sensor 44 such that the temperature of the circulating fluid is adjusted toward the target temperature. The closed loop feedback may take on multiple different forms, such as proportional-integral-derivative (PID) control, any variant thereof (e.g. proportional-integral (PI) control), or still other types of closed loop controls.

In at least one embodiment, controller 42 is programmed to operate in accordance with the algorithms and functions described in commonly assigned, copending U.S. patent application Ser. No. 14/282,383 filed May 20, 2014 by inventors Christopher Hopper et al. and entitled THERMAL CONTROL SYSTEM, the complete disclosure of which is incorporated herein by reference. In other embodiments, controller 42 is programmed to carry out only a subset of the features and algorithms disclosed in the aforementioned '383 patent application. In still other embodiments, controller 42 is programmed to carry out other features and/or algorithms, some of which are not disclosed in the aforementioned '383 patent application.

In some embodiments, control unit 22 includes multiple temperature sensors 44 and controller 42 uses the outputs of the multiple temperature sensors 44 to control the temperature of the circulating fluid. In such embodiments, controller 42 uses the outputs of the multiple temperature sensors 44 to control heat exchanger 30 such that the fluid circulating therethrough has its temperature adjusted (or maintained) to match the target temperature selected by the user. In one such embodiment, controller 42 controls the temperature of the circulating fluid by using both an output temperature value (as measured by a temperature sensor 44 positioned adjacent outlet 40) and a return temperature value (as determined from a temperature sensor 44 positioned adjacent inlet 36). These values may be mathematically combined and/or they may be used as different inputs into the closed-loop feedback algorithm. For example, controller 42 may use the return temperature value as the measured variable in implementing a closed loop proportional-integral (PI) controller for controlling the circulating fluid temperature, and also use the output temperature value to adjust the limits of integration of the PI controller. Other types of controllers may be used in other embodiments for adjusting the temperature of the circulating fluid.

Control unit 22 may also be modified to include one or more flow sensors that measure the rate of fluid flow and report this information to controller 42. In such modified embodiments, controller 42 uses the flow rate in determining what control signals to send to heat exchanger 30.

Circulation path 34 also includes at least one valve 48 (FIG. 1). Valve 48 is in fluid communication with a fluid channel 50 that connects valve 48 to a cartridge receptacle 52 (FIGS. 1 & 2). Cartridge receptacle 52 is dimensioned and shaped to receive cartridge 24. After cartridge 24 is inserted into cartridge receptacle 52, the fluid contained within cartridge 24 is allowed to flow out of cartridge 24 through fluid channel 50 and to valve 48. In one embodiment, valve 48 is a three-way valve that allows the fluid in fluid channel 50 from cartridge 24 to enter circulation path 34 but not leave circulation path 34. In this manner, once fluid from cartridge 24 fills circulation path 34, the fluid is pumped around circulation path 34 without circulating through cartridge 24. Other types of valves 48 may be used.

It will be understood by those skilled in the art that the particular order of the components along circulation path 34 of control unit 22 may be varied from what is shown in FIG. 1. For example, although FIG. 1 depicts pump 38 as being upstream of heat exchanger 30 and valve 48 as being downstream of heat exchanger 30, this order may be changed. Valve 48, pump 38, and temperature sensor 44 may be positioned at any suitable location along circulation path 34. Still further, in some embodiments, a bypass line (not shown) may be added that fluidly couples outlet 40 with inlet 36 such that fluid can circulate along circulation path 34 prior to thermal transfer device 26 being coupled to control unit 22. The bypass line may include a pressure operated valve, a valve controlled by controller 42, a valve controlled by a human operator, or no valve at all. After thermal device 26 is coupled to control unit 22 via hoses 28, fluid flow through the bypass line is cut off or substantially reduced.

Figure 3:
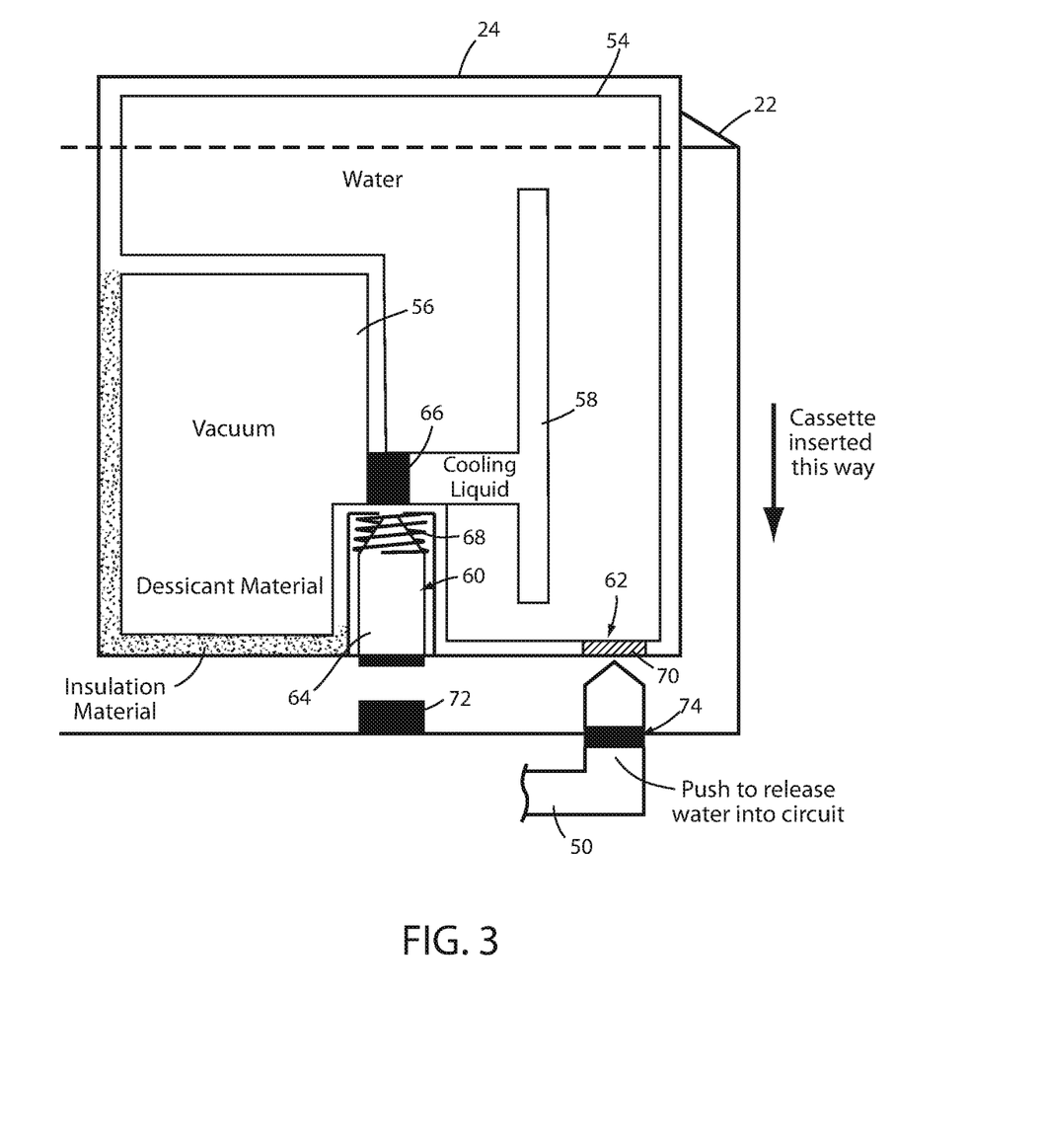
FIG. 3 is a perspective view of one embodiment of a thermal cartridge of the thermal control system of FIG. 1.

FIG. 3 illustrates in greater detail one embodiment of cartridge 24 that may be used with control unit 22. As shown therein, cartridge 24 includes a fluid reservoir 54, a vacuum chamber 56, a coolant chamber 58, a first control 60, and a second control 62. Fluid reservoir 54 contains the fluid that is delivered to circulation path 34 by cartridge 24 when cartridge 24 is inserted into cartridge receptacle 52. In one embodiment, the fluid is water, although it will be understood that other fluids may be used and/or other ingredients may be mixed with the water (e.g. antibacterial and/or antiviral compounds). Fluid reservoir 54, in at least one embodiment, is large enough to hold enough fluid for completely supplying control unit 22 with fluid. In such an embodiment, fluid reservoir 54 is sufficiently large to not only fill circulation path 34, but also hoses 28 and thermal transfer device 26. In an alternative embodiment, control unit 22 includes its own reservoir (not shown) that stores a portion of the fluid used by control unit 22. In still other embodiments, control unit 22 includes a port, or other opening, in which fluid can be added manually, if desired.

Coolant chamber 58 contains a coolant. The particular coolant contained within chamber 58 may vary in different embodiments. In some embodiments, the coolant inside of coolant chamber 58 is an alcohol based coolant. In other embodiments, the coolant is a hydrofluorocarbon, such as HFC-134a (1,1,1,2-tetrafluoroethane) and/or a hydrofluoroolefin, such as HFO-1234yf (2,3,3,3-tetrafluoropropene). Still other types of coolants may be used, as would be known to one of ordinary skill in the art.

In some embodiments, the coolant contained within chamber 58 is maintained at a higher-than-ambient level of pressure (e.g. higher than one atmosphere, or 101.325 kilopascals). In still other embodiments, the coolant is maintained at substantially the same pressure as the ambient pressure. Vacuum chamber 56, in contrast, is maintained at a pressure significantly lower than ambient pressure. In this manner, a pressure difference exists between vacuum chamber 56 and coolant chamber 58. This pressure difference is maintained until first control 60 is activated.

When first control 60 is activated, vacuum chamber 56 and coolant chamber 58 are fluidly coupled such that the higher pressure coolant in coolant chamber 58 flows into the low pressure of vacuum chamber 56. The flow of coolant from coolant chamber 58 into vacuum chamber 56 causes the coolant to evaporate, an endothermic process that draws heat out of the water contained within fluid reservoir 54. The water in fluid reservoir 54 is therefore cooled. In order to ensure more efficient cooling of the fluid in fluid reservoir 54, coolant chamber 58 is constructed, in at least one embodiment, to be substantially completely surrounded by the fluid reservoir 54. Further, the walls defining coolant chamber 58 are constructed to be relatively thin and/or to have relatively low levels of thermal resistance, thereby allowing the heat of the fluid in fluid reservoir 54 to be more easily drawn out.

In at least one embodiment, vacuum chamber 56 includes a desiccant positioned therein to absorb a portion of the coolant from coolant chamber 58, and to thereby facilitate the cooling process. The desiccant may be any suitable hygroscopic material that absorbs the coolant, in either its vapor or fluid state, in an endothermic manner.

In the embodiment shown in FIG. 3, first control 60 comprises a plunger 64 that is adapted to reciprocate in an up-down direction in FIG. 3. Plunger 64 is adapted to selectively dislodge a barrier 66 positioned between coolant chamber 58 and vacuum chamber 56. That is, when plunger 64 is moved upward in FIG. 3, plunger 64 comes into contact with barrier 66 and dislodges barrier 66, thereby allowing coolant from coolant chamber 58 to flow into vacuum chamber 56. A spring 68 may also be provided that urges plunger 64 away from barrier 66 to thereby help ensure barrier 66 is not prematurely dislodged. In the embodiment shown in FIG. 3, control unit 22 includes a projection 72 positioned within cartridge receptacle 52 at a location where it will come into contact with plunger 64 when cartridge 24 is inserted into receptacle 52. Projection 72 is configured to automatically press plunger 64 toward barrier 66 when cartridge 24 is inserted into receptacle 52. In this manner, the cooling of the fluid inside of fluid reservoir 54 commences automatically upon insertion of cartridge 24 into control unit 22.

Second control 62 is adapted to retain fluid within fluid reservoir 54 until after it is chilled by the coolant from coolant chamber 58. Once cooled, second control 62 is further adapted to allow the fluid within fluid reservoir 54 to drain out of reservoir 54 and into circulation path 34. Cartridge 24 is therefore able to provide pre-cooled fluid to control unit 22, thereby providing control unit 22 with a faster ability to provide cooling therapy to a patient.

In the embodiment shown in FIG. 3, second control 62 comprises a seal 70 positioned along an exterior surface of cartridge 24. Seal 70 is adapted to be broken by a push tab 74 integrated into control unit 22. Push tab 74, in turn, is adapted to only break seal 70 when manually pushed by a user. Further, push tab 74 is positioned adjacent fluid channel 50 such that, after seal 70 is broken and push tab 74 is retracted, fluid from within fluid reservoir 54 is able to flow out of reservoir 54. In at least one embodiment, fluid reservoir 54, seal 70, and control unit 22 are designed such that fluid is drawn out of reservoir 54 by gravity. In an alternative embodiment, fluid may be drawn out of fluid reservoir 54 by way of pump 38, or by some other means.

In still another alternative embodiment, push tab 74 is configured to automatically break seal 70 after cartridge 24 is inserted into cartridge receptacle 52. In this alternative embodiment, cartridge 24 may be modified to include a modified first control 60 that is adapted to be manually activated by a user. Such a modification allows a user to first activate first control 60, thereby beginning the cooling of the fluid within fluid reservoir 54, and thereafter release the fluid into control unit 22 when cartridge 24 is inserted therein. In the time between the activation of the modified first control 60 and the insertion of cartridge 24 into cartridge receptacle 52, the expansion of the coolant in vacuum chamber 56 has absorbed sufficient heat from the fluid of reservoir 54 so as to provide a satisfactory amount of cooling to that fluid.

In still another embodiment, the activation of both controls 60 and 62 is carried out automatically upon the insertion of cartridge 24 in control unit 22. This automatic activation may be carried out sequentially after a delay period such that the fluid inside reservoir 54 has sufficient time to cool down before being delivered to control unit 22. In still another alternative embodiment, both control unit 22 and cartridge 24 are modified such that fluid reservoir 54 becomes part of circulation path 34 after cartridge 24 is inserted into control unit 22. In this alternative embodiment, delaying the release of fluid within reservoir 54 after barrier 66 is dislodged may be omitted since the cooling provided by the coolant will continue as the fluid is pumped through circulation path 34.

Vacuum chamber 56 and coolant chamber 58 together define a heat exchanger that is independent of heat exchanger 30 within control unit 22. The heat exchange provided by allowing the coolant to flow out of coolant chamber 58 and into vacuum chamber 56 occurs without the use of electricity. Further, this heat exchange is temporary. That is, coolant chamber 58 and vacuum chamber 56 are not able to provide cooling that lasts longer than the time it takes for coolant to be released out of chamber 58 and into vacuum chamber 56. As a result, in order to maintain the temperature of the fluid released from reservoir 54 at the target temperature (or to further cool the fluid if the coolant does not cool the fluid all the way to the target temperature), control unit 22 utilizes electrical power to run heat exchanger 30, as needed, in order to reach and/or maintain the target temperature.

In those embodiments of control system 20 wherein substantially all of the fluid is drained out of fluid reservoir by way of gravity and/or pump 38, the presence of valve 48 helps ensure that the temperature controlled fluid does not leak out of control unit 22 via any backflow into cartridge 24. In this manner, when cartridge 24 is removed from control unit 22, substantially no fluid loss or spillage occurs. Control unit 22 also includes a drain (not shown) for allowing the fluid within circulation path 34 to be drained after the thermal therapy has been completed.

Thermal control unit 22 may further be modified to include one or more patient temperature probes that are adapted to be attached to one or more locations of thermal interest on a patient, and to measure the patient's temperature at those locations. Such patient temperature probes may be any suitable patient temperature probe that is able to sense the temperature of the patient at the locations of interest. In one embodiment, the patient temperature probes may be conventional Y.S.I. 400 probes marketed by YSI Incorporated of Yellow Springs, Ohio, or probes that are YSI 400 compliant. In other embodiments, different types of probes may be used with thermal control unit 22. Regardless of the specific type of patient temperature probe used in system 20, each temperature probe is connected to a patient temperature probe port (not shown) positioned on control unit 22. Such ports are in electrical communication with controller 42 and controller 42 uses the temperature(s) sensed by one or more of the probes in controlling the temperature of the fluid circulated through control unit 22 and thermal transfer device 26.

When thermal control unit 22 includes one or more ports for receiving one or more patient temperature probes, thermal control unit 22 is configured to operate in at least two different modes that are selectable by a user. In a first mode, known as a manual mode, the thermal control unit 22 controls the temperature of the fluid circulating through control unit 22 and thermal transfer device 26 so that it matches a target temperature chosen by the user. In this mode, the control unit 22 maintains the fluid at the chosen target temperature regardless of the patient's temperature. Indeed, in this manual mode, control unit 22 may be used without any patient temperature probes. In a second mode, known as an automatic mode, the thermal control unit 22 controls the temperature of the fluid circulating through control unit 22 in such a manner that a target patient temperature is achieved and/or maintained. In this automatic mode, at least one patient temperature probe must be coupled to control unit 22 so that control unit 22 knows the patient's current temperature. In the automatic mode, control unit 22 does not necessarily adjust the temperature of the circulating fluid to maintain a constant temperature, but instead makes the necessary temperature adjustments to the fluid in order to effectuate the desired patient temperature. Illustrative examples of these manual and automatic modes are described in more detail in the aforementioned U.S. patent application Ser. No. 14/282,383, which has been incorporated herein by reference.

As described so far herein, heat exchanger 30 has been primarily described as functioning as a chiller. It will be understood, however, that heat exchanger 30 may be constructed in some embodiments to include both a heater and a chiller. Heat exchanger 30 may therefore be capable of both cooling the circulating fluid and heating the circulating fluid. In some instances, where precise temperature control is desired, such heating and cooling may occur at the same time. That is, the circulating fluid may be sequentially both heated and cooled, particularly in instances where the first temperature adjustment overshoots the intended target temperature. In other embodiments, heat exchanger 30 may include only a chiller or only a heater, depending upon the desired type of temperature control. In embodiments where heat exchanger 30 includes both a chiller and a heater, both the heater and the chiller are in communication with, and under the control of, controller 42.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:
1. A thermal control system for controlling a temperature of a patient, the thermal control system comprising:
   a thermal control unit and a cartridge, the thermal control unit comprising:
   a fluid circulation channel including a fluid outlet and a fluid inlet, the fluid outlet adapted to supply fluid to a thermal transfer device and the fluid inlet adapted to receive the fluid back from the thermal transfer device;
   a first heat exchanger;
   a pump for circulating fluid from the fluid inlet, through the first heat exchanger, to the fluid outlet;
   a controller adapted to control the first heat exchanger such that a temperature of the fluid is changed toward a target temperature; and
   a cartridge receptacle adapted to receive the cartridge and to allow fluid from within the cartridge to flow into the fluid circulation channel when the cartridge is inserted into the cartridge receptacle; and
   wherein the cartridge includes a second heat exchanger adapted to change the temperature of the fluid toward the target temperature independent of the first heat exchanger such that the second heat exchanger is able to remove heat from the fluid without the first heat exchanger being activated.

2. The thermal control system of claim 1 wherein the first heat exchanger is electrically powered and the second heat exchanger is not electrically powered.

3. The thermal control system of claim 2 further comprising a battery adapted to supply electrical power to the first heat exchanger.

4. The thermal control system of claim 3 wherein the thermal control unit is portable, the target temperature is lower than the normal human body temperature, and the thermal transfer device is a pad adapted to contact a patient to thereby cool at least a portion of the patient.

5. The thermal control system of claim 2 wherein the second heat exchanger comprises a vacuum and a coolant that are isolated from each other until activated by a user.

6. The thermal control system of claim 1 further comprising a temperature sensor in communication with the controller, the controller adapted to control the first heat exchanger in a closed-loop manner utilizing readings from the temperature sensor in order to change the temperature of the fluid toward the target temperature.

7. A thermal control system for controlling a temperature of a patient, the thermal control system comprising:
 a thermal control unit and a cartridge, the thermal control unit comprising:
 a fluid circulation channel including a fluid outlet and a fluid inlet, the fluid outlet adapted to supply fluid to a thermal transfer device and the fluid inlet adapted to receive the fluid back from the thermal transfer device;
 a first heat exchanger;
 a pump for circulating fluid from the fluid inlet, through the first heat exchanger, to the fluid outlet;
 a controller adapted to control the first heat exchanger such that a temperature of the fluid is changed toward a target temperature; and
 a cartridge receptacle adapted to receive the cartridge and to allow fluid from within the cartridge to flow into the fluid circulation channel when the cartridge is inserted into the cartridge receptacle; and
 wherein the cartridge supplies the fluid for circulating in the fluid circulation channel.

8. The thermal control system of claim 5 wherein, upon activation by the user, the coolant expands into the vacuum and absorbs heat, the coolant being in thermal communication with the fluid such that the coolant absorbs heat from the fluid.

9. The thermal control system of claim 5 further comprising an activation structure that automatically activates the cartridge when the cartridge is inserted into the cartridge receptacle.

10. The thermal control system of claim 7 wherein the cartridge includes a fluid reservoir in which the fluid is stored, and the thermal control unit includes a projection adapted to automatically release fluid from the fluid reservoir into the fluid circulation channel when the cartridge is inserted into the cartridge receptacle.

11. A thermal control system for controlling a temperature of a patient, the system comprising:
 a cartridge comprising a fluid reservoir, a coolant, and a vacuum chamber; and
 a thermal control unit comprising a fluid circulation channel, a heat exchanger, a pump, and a controller; the thermal control unit adapted to receive fluid from the cartridge that has been cooled by the coolant and to pump the cooled fluid to a thermal transfer device in contact with the patient.

12. The thermal control system of claim 11 wherein the controller controls the heat exchanger such that the fluid received from the cartridge has its temperature adjusted toward a target temperature.

13. The thermal control system of claim 12 wherein the thermal control unit is adapted to power the heat exchanger via a battery when the patient is located outside of a medical facility, and to power the heat exchanger via an electrical outlet when the patient is located within a medical facility.

14. The thermal control system of claim 12 wherein the controller controls the heat exchanger by comparing a sensed temperature of the fluid to the target temperature, and using an output of the comparison to control the heat exchanger.

15. The thermal control system of claim 12 wherein the thermal control unit includes a battery and an inductive charging interface adapted to allow the battery to be inductively recharged.

16. The thermal control system of claim 11 wherein the cartridge includes a first control for releasing the coolant into the vacuum chamber, and a second control for releasing the fluid out of the fluid reservoir.

17. The thermal control system of claim 16 wherein the thermal control unit is adapted to automatically activate at least one of the first and second controls when the cartridge is inserted into the thermal control unit.

18. The thermal control system of claim 16 wherein the thermal control unit is adapted to automatically activate both of the first and second controls when the cartridge is inserted into the thermal control unit.

19. A thermal control cartridge comprising:
 a fluid reservoir containing a fluid;
 a coolant;
 a vacuum chamber;
 a first control adapted to maintain the coolant separate from the vacuum chamber until the first control is activated; and
 a second control adapted to maintain the fluid in the fluid reservoir until the second control is activated, wherein the thermal control cartridge is adapted to be inserted into a thermal control unit and to thereafter release the fluid from the fluid reservoir into the thermal control unit.

20. The thermal control cartridge of claim 19 wherein the first control is adapted to be automatically activated upon insertion into the thermal control unit.

21. The thermal control cartridge of claim 19 wherein the activation of the first control causes the coolant to expand into the vacuum chamber, thereby absorbing heat and reducing the temperature of the fluid within the fluid reservoir.

22. The thermal control cartridge of claim 19 wherein the second control is adapted to be automatically activated upon insertion into the thermal control unit.

23. The thermal control cartridge of claim 19 wherein, after the thermal control cartridge has released the fluid into the thermal control unit, the thermal control cartridge is adapted to be removed from the thermal control unit without causing the fluid to leak out of the thermal control unit.

* * * * *